United States Patent
Inazu et al.

(10) Patent No.: US 10,351,502 B2
(45) Date of Patent: *Jul. 16, 2019

(54) METHOD FOR PRODUCING α,α-DIFLUOROACETALDEHYDE

(71) Applicant: Central Glass Company, Limited, Ube-shi, Yamaguchi (JP)

(72) Inventors: Asami Inazu, Kawagoe (JP); Eri Nishizawa, Kawagoe (JP); Shinya Akiba, Kawagoe (JP); Ryo Nadano, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/071,829

(22) PCT Filed: Dec. 1, 2016

(86) PCT No.: PCT/JP2016/085665
§ 371 (c)(1),
(2) Date: Jul. 20, 2018

(87) PCT Pub. No.: WO2017/126233
PCT Pub. Date: Jul. 27, 2017

(65) Prior Publication Data
US 2019/0031587 A1    Jan. 31, 2019

(30) Foreign Application Priority Data

Jan. 21, 2016  (JP) .................................. 2016-009618

(51) Int. Cl.
*C07C 45/41* (2006.01)
*C07C 41/50* (2006.01)
*B01J 31/24* (2006.01)
*C07C 43/317* (2006.01)
*C07C 47/14* (2006.01)
*C07B 61/00* (2006.01)

(52) U.S. Cl.
CPC ............... *C07C 45/41* (2013.01); *B01J 31/24* (2013.01); *B01J 31/2447* (2013.01); *C07C 41/50* (2013.01); *C07C 43/317* (2013.01); *C07C 47/14* (2013.01); *B01J 2523/821* (2013.01); *C07B 61/00* (2013.01)

(58) Field of Classification Search
CPC ................................. C07C 45/41; C07C 41/50
See application file for complete search history.

(56) References Cited

U.S. PATENT DOCUMENTS

| | | |
|---|---|---|
| 2015/0202609 A1 | 7/2015 | Goussev et al. |
| 2015/0329455 A1 | 11/2015 | Ootsuka et al. |
| 2016/0340284 A1 | 11/2016 | Ootsuka et al. |
| 2017/0073298 A1 | 3/2017 | Goussev et al. |

FOREIGN PATENT DOCUMENTS

| | | |
|---|---|---|
| WO | WO 2014/036650 A1 | 3/2014 |
| WO | WO 2014/115801 A1 | 7/2014 |

OTHER PUBLICATIONS

International Search Report (PCT/ISA/210) issued in PCT Application No. PCT/JP2016/085665 dated Dec. 27, 2016 with English translation (five (5) pages).
Japanese-language Written Opinion (PCT/ISA/237) issued in PCT Application No. PCT/JP2016/085665 dated Dec. 27, 2016 with English translation (three (3) pages).
Kaneko S., et al., "A Remarkably Simple Route to Versatile Difluoromethylated Molecules", Journal of Organic Chemistry, 1993, pp. 2302-2312, vol. 58, No. 8 Yokohama, Japan.
Spasyuk D. et al., "Replacing Phosphorus with Sulfur for the Efficient Hydogenation of Esters" Angew. Chem. Ind. Ed., 2013, pp. 2538-2542, vol. 52, Wiley-VCH Verlag GmbH & Co, KGaA, Weinheim.
Greene G. et al., "Protective Groups in Organic Synthesis", John Wiley & Sons, Inc., Third Edition, 1999, A Wiley-Interscience Publication (28 pages).
Dub P. et al., "Air-Stable NNS (ENENES) Ligands and their Well-Defined Ruthenium and Iridium Complexes for Molecular Catalysis" Organmetallics, 2015, pp. 4464-4479, vol. 34, ACS Publication, United States.
Fairweather N. et al., "Homogeneous Hydrogenation of Fatty Acid Methyl Esters and Natural Oils under Neat Conditions", Organometallics, 2015, pp. 335-339, vol. 34, ACS Publication, United States.

*Primary Examiner* — Sikarl A Witherspoon
(74) *Attorney, Agent, or Firm* — Crowell & Moring LLP

(57) ABSTRACT

Disclosed is an industrial method for efficient production of an α,α-difluoroaldehyde compound, which includes reaction of an α,α-difluoroacetate with hydrogen gas ($H_2$) in the presence of a ruthenium catalyst and a base. By the adoption of specific reaction conditions (catalyst, base, pressure etc.), it is possible to produce the target α,α-difluoroaldehyde compound with a high conversion rate and high selectivity.

5 Claims, No Drawings

METHOD FOR PRODUCING α,α-DIFLUOROACETALDEHYDE

FIELD OF THE INVENTION

The present invention relates to a method for producing an α,α-difluoroaldehyde.

BACKGROUND ART

Conventionally known is a method of producing 2,2-difluoroacetaldehyde by reduction of an α,α-difluoroacetate with a hydride reduction agent such as lithium aluminum hydride (see Non-Patent Document 1). On the other hand, the present applicant has filed a patent application on a relevant technique for producing α,α-difluoroacetaldehyde by partial reduction of an α,α-difluoroacetate in the presence of a ruthenium catalyst (see Patent Document 1).

It has further been reported that a ruthenium catalyst used in the present invention is applicable for reduction of esters to alcohols (see Patent Document 2 and Non-Patent Document 2).

PRIOR ART DOCUMENTS

Patent Documents

Patent Document 1: International Publication No. 2014/115801
Patent Document 2: International Publication No. 2014/036650

Non-Patent Documents

Non-Patent Document 1: Journal of Organic Chemistry, 1993, 58, p. 2302-2312
Non-Patent Document 2: Angew. Chem. Int. Ed., 2013, 52, p. 2538-2542

SUMMARY OF THE INVENTION

The method of Non-Patent Document 1, which uses the hydride reduction agent stoichiometrically, is difficult to apply for industrial-scale production due to the facts that: the reduction agent is expensive and needs to be handled with caution; the reduction needs to be performed under very low-temperature conditions (−78° C.) in order to suppress the formation of β,β-difluoroethanol as an overreduction by-product; the method requires complicated post-treatment operation and generates large amounts of wastes. The method of Patent Document 1, which uses the specific ruthenium catalyst, has not yet reached a point where both of high reaction conversion rate and suppression of β,β-difluoroethanol by-production can be achieved because there is a tendency that the selectivity between the aldehyde formed as the target compound and the β,β-difluoroethanol formed sequentially by overreduction of the aldehyde largely varies depending on the conversion rate.

In Patent Document 2 and Non-Patent Document 2, there have been reported examples of reduction reactions of unsubstituted hydrocarbon esters to alcohols with the use of the same ruthenium catalyst as used in the present invention. It is however described in these documents that, although an aldehyde or a hemiacetal thereof is assumed to be formed as an intermediate product of the reduction reaction, the presence of such an aldehyde or hemiacetal has not been proved by $^1$H-NMR analysis of the reaction solution. It is thus unknown whether the aldehyde or its hemiacetal is obtained with high selectivity in the reported reduction reaction.

It is an object of the present invention to provide an industrial method for producing a target aldehyde compound by reduction of an α,α-difluoroacetate with a high conversion rate and high selectivity and with less waste generation while suppressing the formation of an overreduction by-product.

Means for Solving the Problems

As a result of extensive researches made in view of the above circumstances, the present inventors have obtained the following findings.

A ruthenium complex of the formula [2]:

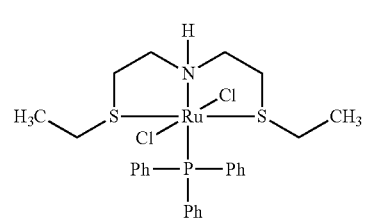

[2]

[in which Ph represents a phenyl group]
(sometimes referred to as "Ru-SNS" in the present specification) serves as a very effective hydrogenation catalyst or its precursor for reduction of
an α,α-difluoroacetate of the general formula [1]:

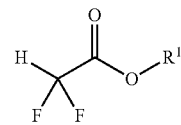

[1]

[in which R$^1$ represents an alkyl group or substituted alkyl group]
so as to achieve not only a high conversion rate but also high selectivity and suppress the formation of β,β-difluoroethanol as a by-product of overreduction of the difluoroacetate, and thus can be used for industrial production with very less waste generation.

The present invention is clearly different from the method of Patent Document 1, in that both of high reaction conversion rate and high selectivity can be achieved. In the method of Patent Document 1, the reaction conversion rate was 28% when the selectivity of α,α-difluoroaldehyde to β,β-difluoroethanol was 92:8 (the details are to be mentioned later); and the reaction conversion rate was 94% when the selectivity of α,α-difluoroaldehyde to β,β-difluoroethanol is 66:34. Although the α,α-difluoroaldehyde can be obtained as a product even in the method of Patent Document 1, the yield of the product was about 20 to 60% (see Comparative Examples 1 and 4).

The present invention has been accomplished based on the findings that, by the adoption of specific reaction conditions (catalyst, base, reaction temperature, hydrogen pressure etc.), it is possible to obtain α,α-difluoroaldehyde as the target compound with a favorable conversion rate of 80% or higher and favorable selectivity of 90% or higher for α,α-difluoroaldehyde and 10% or lower for β,β-difluoroethanol (depending on the reaction conditions, it is possible to obtain the target compound with a conversion rate of 100% and α,α-difluoroaldehyde selectivity of 100%).

The present invention can be used as an alternative to the hydride reduction method that is industrially difficult to implement. In the present invention, the hydrogenation reaction proceeds with a high substrate-to-catalyst ratio; and, after the reaction, the target product can be obtained easily mainly by distillation operation. Further, the load on purification for recovery of starting raw material and separation of by-produced β,β-difluoroethanol can be reduced because of high reaction conversion rate and selectivity. The present invention is very advantageous in that it is possible to provide an industrial method for producing α,α-difluoroaldehyde while solving the conventional problems.

Namely, the present invention provides a method for production of an α,α-difluoroaldehyde compound as defined by the following aspects 1 to 5.

[Inventive Aspect 1]

A method for producing α,α-difluoroacetaldehyde of the formula [3] or an α,α-difluoroacetaldehyde alkyl hemiacetal of the general formula [4], comprising reaction of an α,α-difluoroacetate of the general formula [1] with hydrogen ($H_2$) in the presence of ruthenium complex of the formula [2] and a base,

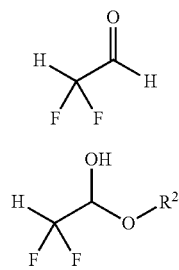

[in which $R^2$ has the same meaning as $R^1$ in the general formula [1]], wherein the reaction is performed under conditions that:

the base is an alkali metal alkoxide and is used in an amount of 0.001 mol or more per 1 mol of the α,α-difluoroacetate; and a pressure of the hydrogen used is 1.0 MPa to 10 MPa (in terms of absolute pressure), whereby a rate of conversion of the α,α-difluoroacetate during the reaction is 80% or higher; and a selectivity of the α,α-difluoroacetaldehyde or α,α-difluoroacetaldehyde alkyl hemiacetal formed from the α,α-difluoroacetate to β,β-difluoroethanol formed as a by-product during the reaction is in a range of α,α-difluoroacetaldehyde or α,α-difluoroacetaldehyde alkyl hemiacetal:β,β-difluoroethanol=90% or higher:10% or lower.

[Inventive Aspect 2]

The method according to Inventive Aspect 1, wherein the alkali metal alkoxide is lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide or potassium tert-butoxide.

[Inventive Aspect 3]

The method according to Inventive Aspect 1 or 2, wherein the alkali metal alkoxide is lithium methoxide, sodium methoxide, potassium methoxide, lithium ethoxide, sodium ethoxide or potassium ethoxide.

[Inventive Aspect 4]

A method for producing α,α-difluoroacetaldehyde or α,α-difluoroacetaldehyde ethyl hemiacetal, comprising reaction of ethyl α,α-difluoroacetate with hydrogen ($H_2$) in the presence of ruthenium complex of the formula [2] and a base, wherein the reaction is performed under conditions that:

the base is sodium ethoxide and is used in an amount of 0.01 to 5.0 mol per 1 mol of the ethyl α,α-difluoroacetate; and a pressure of the hydrogen used is 2.0 MPa to 6.0 MPa (in terms of absolute pressure), whereby a rate of conversion of the ethyl α,α-difluoroacetate during the reaction is 90% or higher; and a selectivity of the α,α-difluoroacetaldehyde or α,α-difluoroacetaldehyde ethyl hemiacetal formed from the ethyl α,α-difluoroacetate to β,β-difluoroethanol formed as a byproduct during the reaction is in a range of α,α-difluoroacetaldehyde or α,α-difluoroacetaldehyde ethyl hemiacetal:β,β-difluoroethanol=93% or higher:7% or lower.

[Inventive Aspect 5]

The method according to any one of Inventive Aspects 1 to 4, wherein the reaction is performed by the use of an alcohol solvent at a reaction temperature of 30° C. or lower.

Effects of the Invention

It is possible according to the present invention to produce the target α,α-difluoroaldehyde compound with a high conversion rate and high selectivity by the use of the readily available raw material as compared with the conventional methods.

DETAILED DESCRIPTION OF THE EMBODIMENTS

Hereinafter, the present invention will be described in detail below. It should be noted that: the scope of the present invention is not limited to the following embodiments; and various changes and modifications of the following embodiments can be made as appropriate, based on the general knowledge of those skilled in the art, within the range that does not depart from the scope of the present invention.

In the present invention, the α,α-difluoroacetaldehyde of the formula [3] or the α,α-difluoroacetaldehyde alkyl hemiacetal of the general formula [4] is produced by reacting the α,α-difluoroacetate of the general formula [1] with hydrogen ($H_2$) in the presence of the ruthenium complex of the formula [2] and the base under the above-mentioned reaction conditions. (In the present specification, the α,α-difluoroacetaldehyde or α,α-difluoroacetaldehyde alkyl hemiacetal as the target product is sometimes simply referred to as "α,α-difluoroacetaldehyde compound".)

In the α,α-difluoroacetate of the general formula [1], $R^1$ represents a substituted or unsubstituted alkyl group. The unsubstituted alkyl group is generally a $C_1$-$C_{18}$ alkyl group having a straight-chain structure, a branched structure or a cyclic structure (in the case of 3 or more carbons). Among others, a $C_1$-$C_{10}$ straight-chain or branched alkyl group and a $C_3$-$C_{12}$ cyclic alkyl group are preferred. Examples of the unsubstituted alkyl group methyl, ethyl, n-propyl, i-propyl, n-butyl, i-butyl, s-butyl, t-butyl, n-pentyl, cyclopropyl, cyclobutyl, cyclopentyl, cyclohexyl, cycloheptyl, norbornyl and adamantyl.

Examples of the substituted alkyl group are those obtained by substitution of any number of and any combination of substituents onto any of carbon atoms of the above unsubstituted alkyl groups. As such substituents, there can be used: halogen atoms such as fluorine, chlorine and bromine; lower alkyl groups such as methyl, ethyl and propyl; lower haloalkyl groups such as fluoromethyl, chloromethyl and bromomethyl; lower alkoxy groups such as methoxy, ethoxy and propoxy; lower haloalkoxy groups such as fluoromethoxy, chloromethoxy and bromomethoxy; cyano group; lower alkoxycarbonyl groups such as methoxycarbonyl, ethoxycarbonyl and propoxycarbonyl; carboxyl group; protected carboxyl groups; amino group; protected amino groups; hydroxyl group; and protected hydroxyl groups. Depending on the kind of the substituent group, the substituent group itself may be involved in a side reaction. It is however feasible to minimize the side reaction by the adoption of the suitable reaction conditions.

In the present specification, the term "lower" means that the group to which the term is attached has 1 to 6 carbon atoms in the form of a straight-chain structure, a branched structure or a cyclic structure (in the case of 3 or more carbons). As the protecting groups of the carboxyl, amino and hydroxyl groups, there can be used any of those described in "Protective Groups in Organic Synthesis", Third Edition, 1999, John Wiley & Sons, Inc. Preferred examples of the protecting groups are alkyl groups such as methyl.

Among the α,α-difluoroacetate of the general formula [1], preferred are methyl α,α-difluoroacetate and ethyl α,α-difluoroacetate, both of which are readily available on a large scale.

The ruthenium complex used in the present invention can be prepared by e.g. a method disclosed in Patent Document 2 or can be a commercially available product.

It suffices to use the ruthenium complex of the formula [2] in an amount of 0.000001 mol or more per 1 mol of the α,α-difluoroacetate of the general formula [1]. The amount of the ruthenium complex used is preferably 0.00001 to 0.005 mol, more preferably 0.00003 to 0.002 mol, per 1 mol of the α,α-difluoroacetate.

As the base, an alkali metal alkoxide is used. Examples of the alkali metal alkoxide are lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide and potassium tert-butoxide. Among others, lithium methoxide, sodium methoxide, potassium methoxide, lithium ethoxide, sodium ethoxide, potassium ethoxide, lithium isopropoxide, sodium isopropoxide and potassium isopropoxide are preferred. Particularly preferred are lithium methoxide, sodium methoxide, potassium methoxide, lithium ethoxide, sodium ethoxide and potassium ethoxide.

It suffices to use the base in an amount of 0.001 mol or more per 1 mol of the α,α-difluoroacetate of the general formula [1]. The amount of the base used is preferably 0.005 to 10 mol, more preferably 0.01 to 5 mol, per 1 mol of the α,α-difluoroacetate.

It is assumed that the true catalytic active species is derived from the ruthenium complex of the formula [2] as required in the presence of the base. Thus, the case where the catalytic active species (including isolated form) is prepared in advance and used in the hydrogenation reaction is included in the scope of the present invention.

It suffices to use the hydrogen ($H_2$) in an amount of 1 mol or more per 1 mol of the α,α-difluoroacetate of the general formula [1]. Preferably, the hydrogen is used in a large excessive amount. It is particularly preferable to use the hydrogen in a large excessive amount under pressurized conditions.

The hydrogen pressure is generally 1.0 to 10 MPa (in terms of absolute pressure; the same applies to the following), preferably 2.0 to 6.0 MPa, more preferably 2.0 to 5.0 MPa.

In the production method of the present invention, the reaction can be performed by the use of a solvent. There is no particular limitation on the reaction solvent used. Examples of the reaction solvent are aliphatic hydrocarbons (such as n-pentane, n-hexane and n-heptane), aromatic hydrocarbons (such as benzene, toluene and xylene), nitriles (such as acetonitrile, propionitrile, phenylacetonitrile, isobutyronitrile and benzonitrile), halogenated compounds (such as methylene chloride and 1,2-dichloroethane), acid amides (such as dimethylformamide, dimethylacetamide, methylformamide, formamide, hexamethylphosphoric triamide and N-methylpyrrolidone), lower ethers (such as diethyl ether, tetrahydrofuran, 1,2-dimethoxyethane, 1,4-dioxane, 1,2-epoxyethane, 1,4-dioxane, dibutyl ether, t-butyl methyl ether and substituted tetrahydrofuran) and alcohols (such as methanol, ethanol, n-propanol, isopropanol, n-butanol, tert-butanol, n-pentanol, n-hexanol and cyclohexanol). Among others, ethers and alcohols are preferred. Alcohols are more preferred. These reaction solvents can be used solely or in combination thereof. In the production of the target α,α-difluoroaldehyde compound, methanol, ethanol and n-propanol are particularly preferred because these alcohols are easy to separate by fractional distillation.

It suffices to use the reaction solvent in an amount of 0.03 L (liter) or more per 1 mol of the α,α-difluoroacetate of the general formula [1]. The amount of the reaction solvent used is preferably 0.05 to 10 L, more preferably 0.07 to 7 L, per 1 mol of the α,α-difluoroacetate.

In the case of using an alcohol solvent, the reaction temperature is generally +30° C. or lower, preferably +25 to -30° C., more preferably +25 to -10° C., still more preferably +25 to 0° C. In the case of using an aliphatic hydrocarbon solvent, aromatic hydrocarbon solvent, halogenated solvent or ether solvent, the reaction temperature is generally +50° C. or lower, preferably +45 to -30° C., more preferably +40 to -20° C., still more preferably +35 to -10° C. In order to make the best possible use of the present invention, it is particularly preferable to perform the reaction by the use of an alcohol solvent at a reaction temperature of 25° C. or lower.

In the present invention, the hydrolysis of the α,α-difluoroacetate as the raw substrate material is influenced by water contained in the solvent or base. It is thus preferable that the amount of water contained in the solvent or base is as small as possible. It suffices that the amount of water in the mixed reaction system of the catalyst, solvent, base and raw substrate material is 10 to 0.001 mass %. The amount of water in the reaction system is preferably 5 to 0.001 mass %, more preferably 0.5 to 0.001 mass %.

As the α,α-difluoroacetaldehyde of the formula [3] is an aldehyde having a strong electron-attracting group directly bonded thereto, it is often the case that the α,α-difluoroacetaldehyde is obtained in the form of a hemiacetal. (As a matter of course, the α,α-difluoroacetaldehyde can be obtained in aldehyde form.) In the present invention, for example, the α,α-difluoroacetaldehyde alkyl hemiacetal of the general formula [4] can be obtained as a stable equivalent of the α,α-difluoroacetaldehyde.

The alcohol function of the hemiacetal is derived from the alkali metal alkoxide used as the base, the alcohol used as the reaction solvent and the ester moiety of the raw substrate material.

For production of the α,α-difluoroaldehyde or the α,α-difluoroaldehyde alkyl hemiacetal of the general formula [4] in the present invention, the α,α-difluoroacetate is reacted with hydrogen (H$_2$) in the presence of the ruthenium complex of the formula [2] and the base under the specific reaction conditions that: the alkali metal alkoxide is used as the base in an amount of 0.001 mol or more per 1 mole of the α,α-difluoroacetate; and the hydrogen pressure is 1.0 MPa to 10 MPa. By this reaction, the target α,α-difluoroaldehyde compound is obtained with such favorable results that: the rate of conversion of the α,α-difluoroacetate is 80% or higher; and the selectivity of the α,α-difluoroacetaldehyde compound formed from the α,α-difluoroacetate to by-produced β,β-difluoroethanol is 90% or higher:10% or lower (assuming the sum of the α,α-difluoroacetate compound and β,β-difluoroethanol as 100).

It is a preferred embodiment of the present invention to perform the reaction at a hydrogen pressure of 2.0 MPa to 6.0 MPa by using sodium ethoxide or potassium ethoxide as the alkali metal alkoxide in an amount of 0.005 to 10 mol per 1 mol of the α,α-difluoroacetate. In this case, the α,α-difluoroacetaldehyde compound is produced such that: the rate of conversion of the α,α-difluoroacetate is 90%; and the selectivity of the α,α-difluoroacetaldehyde compound formed from the α,α-difluoroacetate to the β,β-difluoroethanol formed as the by-product is 93% or higher:7% or lower.

It is a more preferred embodiment of the present invention to perform the reaction at a hydrogen pressure of 2.0 MPa to 5.0 MPa by using sodium ethoxide or potassium ethoxide as the alkali metal alkoxide in an amount of 0.01 to 5 mol per 1 mol of the α,α-difluoroacetate. In this case, the α,α-difluoroacetaldehyde compound is produced with such very favorable results that: the rate of conversion of the α,α-difluoroacetate is 93%; and the selectivity of the α,α-difluoroacetaldehyde compound formed from the α,α-difluoroacetate to the β,β-difluoroethanol formed as the by-product is 95% or higher:5% or lower (see Examples 1 to 5, Examples 7 to 9 and Examples 11 to 14 mentioned later).

The conversion rate and selectivity can be determined by monitoring the progress of the reaction with any analytical means such as gas chromatography, liquid chromatography or NMR. It is preferable to determine the time at which there is seen almost no decrease of the raw substrate material as the end of the reaction.

The reaction time is generally 72 hours or less. As the reaction time is varied depending on the kind of the raw substrate material and the reaction conditions, it is preferable to perform the reaction until there is seen almost no decrease of the raw substrate material by monitoring the progress of the reaction by various analytical means as mentioned above.

By the adoption of the above-mentioned conditions, the target α,α-difluoroacetaldehyde compound is obtained in such a manner that: the conversion rate is 80% or higher; and the selectivity of α,α-difluoroacetaldehyde to by-produced β,β-difluoroethanol is 90% or higher:10% or lower. When the target α,α-difluoroacetaldehyde compound is obtained with a high purity, there is no need to perform purification operation such as high-theoretical-plate fractional distillation for purification of the target compound. The achievement of high selectivity as disclosed in the after-mentioned working examples leads to the reduction of time and effort of the after-mentioned purification operation. The present invention is hence very advantageous for industrial production.

The reaction container used in the present invention can be of any material resistant to heat and resistant to corrosion by hydrogen fluoride, hydrogen chloride etc. Stainless steel, Hastelloy, Monel and platinum are preferred as the material of the reaction container. The reaction may be formed of a material with a lining of the above metal material.

The α,α-difluoroaldehyde compound is obtained by ordinary post-treatment process for organic synthesis. In the post-treatment process after the reaction, the α,α-difluoroaldehyde compound can be purified to a higher purity, as required, by activated carbon treatment, fractional distillation, recrystallization, column chromatography etc. In the case where the boiling point of the target compound is low, it is convenient to recover the target compound by direct distillation from the reaction completed solution. In the reaction system where the base is present, the target compound (self-polymerization product, hydrate, hemicacetal etc.) of relatively high acidity tends to form a salt or complex with the base and remain in the distillation residue after the above recovery distillation. In such a case, the target compound can be recovered with high yield by neutralizing the reaction completed solution with an organic acid such as formic acid, acetic acid, citric acid, oxalic acid, benzoic acid, methanesulfonic acid or paratoluenesulfonic acid, or an inorganic acid such as hydrogen chloride, hydrogen bromide, nitric acid or sulfuric acid, and subjecting the neutralized reaction completed solution to recovery distillation (including washing the distillation residue with an organic solvent such as diisopropyl ether).

Among the α,α-difluoroaldehyde compound, the α,α-difluoroaldehyde alkyl hemiacetal is a hemiacetal of the α,α-difluoroaldehyde and thus can be said as an equivalent of the α,α-difluoroaldehyde. Naturally, the α,α-difluoroaldehyde compound may be obtained in any equivalent form, other than α,α-difluoroaldehyde alkyl hemiacetal, such as a self-polymerization product, a hydrate, a compound with a combination structure thereof or the like.

In the case where an α,α-difluoroaldehyde alkyl hemiacetal-derived dimer of the general formula [5] is obtained as a stable equivalent of the α,α-difluoroaldehyde of the formula [3]

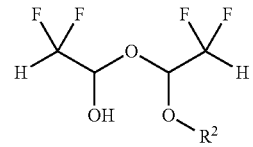

[in which R$^2$ has the same meaning as R2 in the general formula [4]], it is feasible to purify the dimer to α,α-difluoroaldehyde hemiacetal by bringing the dimer into contact with methanol or ethanol in the post-treatment process.

EXAMPLES

The present invention will be described in more detail below by way of the following examples. It should be understood that the following examples are illustrative and are not intended to limit the present invention thereto. In the following description, the abbreviations Ph and Et refer to phenyl and ethyl, respectively.

Examples 1 to 14 and Comparative Examples 1 to 8

In Examples 1 to 14 and Comparative Examples 1 to 8, production experiments were carried out by the following general production process.

Into a pressure-proof reaction container of stainless steel (SUS), a predetermined amount (1 eq) of α,α-difluoroacetate of the following formula:

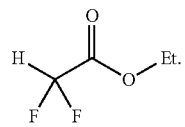

a predetermined amount of ruthenium complex of the following formula:

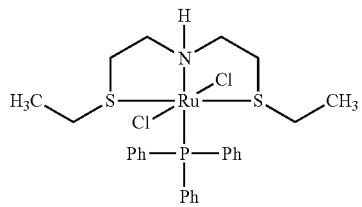

(purity: 97%; available from Sigma-Aldrich Co. LLC.) or ruthenium complex of the following formula:

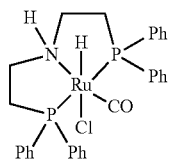

(purity: >90%, available as Ru-MACHO™ from Takasago International Corporation), a predetermined amount of base and a predetermined amount of reaction solvent. The inside of the reaction container was replaced three times with hydrogen gas. The hydrogen pressure inside the reaction container was set to a predetermined pressure value. Subsequently, the contents of the reaction container were reacted with stirring for a predetermined reaction time at a predetermined reaction temperature. The resulting reaction completed solution was analyzed by $^{19}$F-NMR. Based on the analysis results, the conversion rate and the selectivity of α,α-difluoroacetaldehyde ethyl hemiacetal of the following formula: (as a stable α,α-difluoroacetaldehyde equivalent)

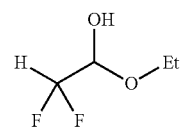

to β,β-difluoroethanol of the following formula:

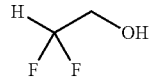

formed as an overreduction product were determined. The $^1$H- and $^{19}$F-NMR data and gas chromatographic data of the thus-obtained α,α-difluoroacetaldehyde ethyl hemiacetal were in agreement with those of the reference standard.

Comparative Example 9

Into a pressure-proof reaction container of stainless steel (SUS), 50 g (320 mmol, 1 eq) of ethyl 3,3,3-trifluoropropionate of the following formula:

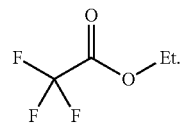

0.27 g (0.043 mmol, 0.0001 eq) of ruthenium complex of the following formula:

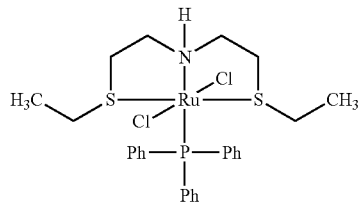

(purity: 97%; available from Aldrich Co. LLC.), 5.4 g (80 mmol, 0.25 eq) of sodium ethoxide and 64 mL (5.0 mol/L) of ethanol were put. The inside of the reaction container was replaced three times with hydrogen gas. The hydrogen pressure inside the reaction container was set to 3.0 MPa. Subsequently, the contents of the reaction container were reacted with stirring for 6 hours at 30° C. When the resulting reaction completed solution was analyzed by $^{19}$F-NMR, it was confirmed that only ethyl 3,3,3-trifluoropropionate as the raw material was present.

The results of Examples 1 to 14 and Comparative Examples 1-8 were summarized as follows in TABLE 1.

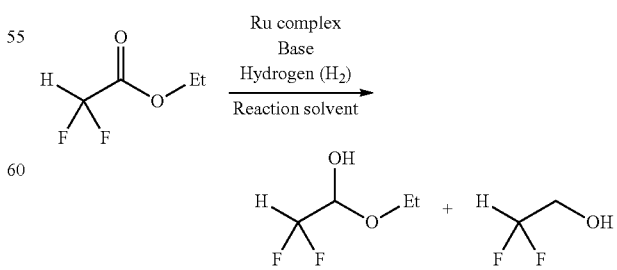

TABLE 1

| Ex. No. | Amount of α,α-Difluoroacetate | Kind of ruthenium complex | Amount of ruthenium complex | Kind and amount of base | Kind and amount of reaction solvent |
|---|---|---|---|---|---|
| Ex. 1 | 50 g (0.403 mol) | Ru-SNS | 0.034 g (0.054 mmol) | sodium ethoxide 13.7 g (0.201 mol) | ethanol 202 mL (2.0 mol/L) |
| Ex. 2 | 50 g (0.403 mol) | Ru-SNS | 0.025 g (0.040 mmol) | sodium ethoxide 13.7 g (0.201 mol) | ethanol 202 mL (2.0 mol/L) |
| Ex. 3 | 50 g (0.403 mol) | Ru-SNS | 0.017 g (0.027 mmol) | sodium ethoxide 13.7 g (0.201 mol) | ethanol 202 mL (2.0 mol/L) |
| Ex. 4 | 50 g (0.403 mol) | Ru-SNS | 0.025 g (0.040 mmol) | sodium ethoxide 11.0 g (0.161 mol) | ethanol 202 mL (2.0 mol/L) |
| Ex. 5 | 50 g (0.403 mol) | Ru-SNS | 0.034 g (0.054 mmol) | potassium ethoxide 8.48 g (0.101 mol) | ethanol 202 mL (2.0 mol/L) |
| Ex. 6 | 25 g (0.201 mol) | Ru-SNS | 0.017 g (0.027 mmol) | lithium ethoxide 2.6 g (0.050 mol) | ethanol 101 mL (2.0 mol/L) |
| Ex. 7 | 25 g (0.201 mol) | Ru-SNS | 0.017 g (0.027 mmol) | sodium ethoxide 6.8 g (0.101 mol) | ethanol 402 mL (0.5 mol/L) |
| Ex. 8 | 10 g (0.081 mol) | Ru-SNS | 0.007 g (0.011 mmol) | sodium ethoxide 21.9 g (0.322 mol) | ethanol 111 mL (0.7 mol/L) |
| Ex. 9 | 50 g (0.403 mol) | Ru-SNS | 0.025 g (0.040 mmol) | sodium ethoxide 13.7 g (0.201 mol) | ethanol 202 mL (2.0 mol/L) |
| Ex. 10 | 50 g (0.403 mol) | Ru-SNS | 0.034 g (0.054 mmol) | sodium ethoxide 6.9 g (0.101 mol) | ethanol 203 mL (2.0 mol/L) |
| Ex. 11 | 50 g (0.403 mol) | Ru-SNS | 0.017 g (0.027 mmol) | sodium ethoxide 13.7 g (0.201 mol) | ethanol 202 mL (2.0 mol/L) |
| Ex. 12 | 50 g (0.403 mol) | Ru-SNS | 0.025 g (0.040 mmol) | sodium ethoxide 13.7 g (0.201 mol) | ethanol 202 mL (2.0 mol/L) |
| Ex. 13 | 50 g (0.403 mol) | Ru-SNS | 0.017 g (0.027 mmol) | sodium ethoxide 13.7 g (0.201 mol) | ethanol 202 mL (2.0 mol/L) |
| Ex. 14 | 50 g (0.403 mol) | Ru-SNS | 0.017 g (0.027 mmol) | sodium ethoxide 13.7 g (0.201 mol) | ethanol 81 mL (5.0 mol/L) |
| Comp. Ex. 1 | 109 g (0.878 mol) | Ru-MACHO | 0.071 g (0.117 mmol) | sodium methoxide 28.6 g (0.527 mol) | methanol 360 mL (2.4 mol/L) |
| Comp. Ex. 2 | 109 g (0.878 mol) | Ru-MACHO | 0.071 g (0.117 mmol) | sodium methoxide 2.2 g (0.04 mol) | methanol 360 mL (2.4 mol/L) |
| Comp. Ex. 3 | 109 g (0.878 mol) | Ru-MACHO | 0.071 g (0.117 mmol) | sodium methoxide 11.9 g (0.220 mol) | methanol 360 mL (2.4 mol/L) |
| Comp. Ex. 4 | 109 g (0.878 mol) | Ru-MACHO | 0.107 g (0.176 mmol) | sodium methoxide 11.9 g (0.22 mol) | ethanol 360 mL (2.4 mol/L) |
| Comp. Ex. 5 | 50 g (0.403 mol) | Ru-SNS | 0.034 g (0.054 mmol) | sodium hydroxide 4.0 g (0.100 mol) | ethanol 203 mL (2.0 mol/L) |
| Comp. Ex. 6 | 50 g (0.403 mol) | Ru-SNS | 0.034 g (0.054 mmol) | potassium hydroxide 5.6 g (0.100 mol) | ethanol 203 mL (2.0 mol/L) |
| Comp. Ex. 7 | 50 g (0.403 mol) | Ru-SNS | 0.034 g (0.054 mmol) | potassium fluoride 6.0 g (0.103 mol) | ethanol 203 mL (2.0 mol/L) |
| Comp. Ex. 8 | 50 g (0.403 mol) | Ru-SNS | 0.034 g (0.054 mmol) | pyridine 8.1 g (0.102 mol) | ethanol 203 mL (2.0 mol/L) |

| Ex. No. | Reaction temp. | Reaciton time | Conversion rate | Selectivity*[1] | Pressure |
|---|---|---|---|---|---|
| Ex. 1 | 25° C. | 4 hr | 100 | 98:2 | 3 MPa |
| Ex. 2 | 25° C. | 6 hr | 100 | 98:2 | 3 MPa |
| Ex. 3 | 25° C. | 6 hr | 96 | 98:2 | 3 MPa |
| Ex. 4 | 25° C. | 6 hr | 97 | 97:3 | 3 MPa |
| Ex. 5 | 25° C. | 6 hr | 93 | 95:5 | 3 MPa |
| Ex. 6 | 25° C. | 6 hr | 82 | 90:10 | 3 MPa |
| Ex. 7 | 25° C. | 6 hr | 100 | 97:3 | 3 MPa |
| Ex. 8 | 25° C. | 6 hr | 100 | 100:0 | 2.5 MPa |
| Ex. 9 | 25° C. | 6 hr | 98 | 96:4 | 2.5 MPa |
| Ex. 10 | 25° C. | 6 hr | 98 | 91:9 | 4.5 MPa |
| Ex. 11 | 25° C. | 6 hr | 99 | 97:3 | 4.5 MPa |
| Ex. 12 | 25° C. | 4 hr | 100 | 96:4 | 2.5 MPa |
| Ex. 13 | 25° C. | 6 hr | 99 | 97:3 | 2.5 MPa |
| Ex. 14 | 25° C. | 6 hr | 97 | 96:4 | 2.5 MPa |
| Comp. Ex. 1 | 25° C. | 6 hr | 94 | 66:34 | 4.5 MPa |
| Comp. Ex. 2 | 10° C. | 6 hr | 69 | 81:19 | 3 MPa |
| Comp. Ex. 3 | 25° C. | 6 hr | 97 | 0:100 | 4.5 MPa |
| Comp. Ex. 4 | 10° C. | 6 hr | 28 | 92:8 | 3 MPa |
| Comp. Ex. 5 | 25° C. | 6 hr | 0 | — | 3 MPa |
| Comp. Ex. 6 | 25° C. | 6 hr | 0 | — | 3 MPa |
| Comp. Ex. 7 | 25° C. | 6 hr | 0 | — | 3 MPa |
| Comp. Ex. 8 | 25° C. | 6 hr | 0 | — | 3 MPa |

*[1]The selectivity refers to the ratio of α,α-difluoroaldehyde compound (target product):β,β-difluoroethanol (by-product) assuming that the sum of both product compounds as 100

INDUSTRIAL APPLICABILITY

The α,α-difluoroaldehyde compound produced by the production method of the present invention is usable as an intermediate for pharmaceutical and agrichemical products.

The invention claimed is:

1. A method for producing an α,α-difluoroacetaldehyde of the formula [3] or α,α-difluoroacetaldehyde alkyl hemiacetal of the general formula [4], comprising reaction of an α,α-difluoroacetate of the general formula [1] with hydrogen in the presence of a ruthenium complex of the formula [2] and a base,

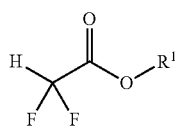
[1]

in which R¹ represents an alkyl group or substituted alkyl group,

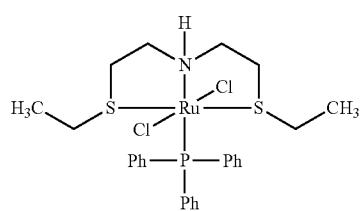
[2]

in which Ph represents a phenyl group,

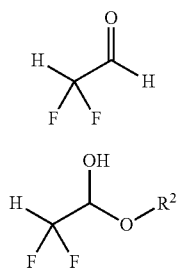
[3]

[4]

in which R² has the same meaning as R¹ in the general formula [1], wherein the reaction is performed under conditions that:
the base is an alkali metal alkoxide and is used in an amount of 0.001 mol or more per 1 mol of the α,α-difluoroacetate; and
a pressure the hydrogen used is 1.0 MPa to 10 MPa in terms of absolute pressure,
whereby a rate of conversion of the α,α-difluoroacetate during the reaction is 80% or higher; and a selectivity of the α,α-difluoroacetaldehyde or α,α-difluoroacetaldehyde alkyl hemiacetal formed from the α,α-difluoroacetate to β,β-difluoroethanol formed as a by-product during the reaction is in a range of α,α-difluoroacetaldehyde or α,α-difluoroacetaldehyde alkyl hemiacetal:β,β-difluoroethanol=90% or higher:10% or lower.

2. The method according to claim 1, wherein the alkali metal alkoxide is lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide or potassium tert-butoxide.

3. The method according to claim 2, wherein the alkali metal alkoxide is lithium methoxide, sodium methoxide, potassium methoxide, lithium ethoxide, sodium ethoxide or potassium ethoxide.

4. The method according to claim 1,
wherein the α,α-difluoroacetate of the general formula [1] is ethyl α,α-difluoroacetate
wherein the α,α-difluoroacetaldehyde alkyl hemiacetal of the general formula [4] is α,α-difluoroacetaldehyde ethyl hemiacetal,
wherein the base is sodium ethoxide and is used in an amount of 0.01 to 5.0 mol per 1 mol of the ethyl α,α-difluoroacetate;
wherein the pressure of the hydrogen used is 2.0 MPa to 6.0 MPa in terms of absolute pressure,
wherein the rate of conversion of the ethyl α,α-difluoroacetate during the reaction is 90% or higher; and
wherein the selectivity of the α,α-difluoroacetaldehyde or α,α-difluoroacetaldehyde ethyl hemiacetal formed from the ethyl α,α-difluoroacetate to β,β-difluoroethanol formed as a byproduct during the reaction is in a range of α,α-difluoroacetaldehyde or α,α-difluoroacetaldehyde ethyl hemiacetal:β,β-difluoroethanol=93% or higher:7% or less.

5. The method according to claim 1, wherein the reaction is performed by the use of an alcohol solvent at a reaction temperature of 30° C. or lower.

* * * * *